United States Patent
Ostroff

(10) Patent No.: US 6,954,670 B2
(45) Date of Patent: Oct. 11, 2005

(54) SIMPLIFIED DEFIBRILLATOR OUTPUT CIRCUIT

(75) Inventor: Alan H. Ostroff, San Clemente, CA (US)

(73) Assignee: Cameron Health, Inc., San Clemente, CA (US)

(*) Notice: Subject to any disclaimer, the term of this patent is extended or adjusted under 35 U.S.C. 154(b) by 584 days.

(21) Appl. No.: 10/011,957

(22) Filed: Nov. 5, 2001

(65) Prior Publication Data

US 2003/0088283 A1 May 8, 2003

(51) Int. Cl.$^7$ ................................................ A61N 1/39
(52) U.S. Cl. ........................................................... 607/5
(58) Field of Search ................................ 607/1–2, 4–5, 607/142

(56) References Cited

U.S. PATENT DOCUMENTS

| | | |
|---|---|---|
| 3,653,387 A | 4/1972 | Ceier |
| 3,710,374 A | 1/1973 | Kelly |
| 4,191,942 A | 3/1980 | Long |
| 4,223,678 A | 9/1980 | Langer et al. |
| 4,402,322 A | 9/1983 | Duggan |
| 4,407,288 A | 10/1983 | Langer et al. |
| 4,602,637 A | 7/1986 | Elmqvist et al. |
| 4,800,883 A | 1/1989 | Winstrom |
| 4,830,005 A | 5/1989 | Woskow |
| 5,109,842 A | 5/1992 | Adinolfi |
| 5,129,392 A | 7/1992 | Bardy et al. |
| 5,144,946 A | 9/1992 | Weinberg et al. |
| 5,184,616 A | 2/1993 | Weiss |
| 5,331,966 A | 7/1994 | Bennett et al. |
| 5,376,103 A | 12/1994 | Anderson et al. |
| 5,376,104 A | 12/1994 | Sakai et al. |
| 5,411,547 A | 5/1995 | Causey, III |
| 5,413,591 A | 5/1995 | Knoll |
| 5,431,684 A * | 7/1995 | Archer et al. ................. 607/5 |
| 5,507,781 A | 4/1996 | Kroll et al. |
| 5,531,765 A | 7/1996 | Pless |
| 5,601,607 A | 2/1997 | Adams |
| 5,645,572 A * | 7/1997 | Kroll et al. ................... 607/5 |
| 5,658,317 A | 8/1997 | Haefner et al. |
| 5,674,260 A | 10/1997 | Weinberg |
| 5,690,683 A | 11/1997 | Haefner et al. |
| 5,697,953 A | 12/1997 | Kroll et al. |
| 5,713,926 A | 2/1998 | Hauser et al. |
| 5,718,242 A | 2/1998 | McClure et al. |
| 5,766,226 A | 6/1998 | Pedersen |
| 5,836,976 A | 11/1998 | Min et al. |
| 5,919,211 A | 7/1999 | Adams |
| 5,935,154 A | 8/1999 | Westlund |

(Continued)

FOREIGN PATENT DOCUMENTS

| | | |
|---|---|---|
| EP | 0316616 A2 | 5/1989 |
| EP | 0347353 A1 | 12/1989 |

(Continued)

OTHER PUBLICATIONS

Olson, Walter H. et al. "Onset and Stability for Ventricular Tachyarrhythmia Detection in an Implantable Pacer–Cardioverter–Defibrillator," *IEEE* (1987) pp. 167–170.

(Continued)

*Primary Examiner*—Kennedy Schaetzle
*Assistant Examiner*—Kristen Mullen
(74) *Attorney, Agent, or Firm*—Crompton, Seager & Tufte, LLC

(57) ABSTRACT

High side driver circuitry for a defibrillator circuit employs respective capacitors connected to respective gates of silicon controlled rectifiers serving as high side switches. Applying a voltage pulse to a selected capacitor turns on the associated SCR. Positive turn-on of the high side SCRs is insured by inserting a constant current source into the low side activation current path at start-up.

40 Claims, 2 Drawing Sheets

U.S. PATENT DOCUMENTS

| | | |
|---|---|---|
| 5,941,904 A | 8/1999 | Johnston et al. |
| 6,014,586 A | 1/2000 | Weinberg et al. |
| 6,026,325 A | 2/2000 | Weinberg et al. |
| 6,058,328 A | 5/2000 | Levine et al. |
| 6,096,063 A | 8/2000 | Lopin et al. |
| 6,128,531 A | 10/2000 | Campbell-Smith |
| 6,144,866 A | 11/2000 | Miesel et al. |
| 6,169,921 B1 | 1/2001 | KenKnight et al. |
| 6,185,450 B1 | 2/2001 | Seguine et al. |
| 6,208,895 B1 | 3/2001 | Sullivan et al. |
| 6,241,751 B1 | 6/2001 | Morgan et al. |
| 6,411,844 B1 | 6/2002 | Kroll et al. |
| 2001/0027330 A1 | 10/2001 | Sullivan et al. |

FOREIGN PATENT DOCUMENTS

| | | |
|---|---|---|
| EP | 0518599 B1 | 6/1992 |
| EP | 0518599 A2 | 6/1992 |
| EP | 0536873 B1 | 7/1992 |
| EP | 0641573 A2 | 8/1994 |
| EP | 0641573 A3 | 8/1994 |
| EP | 0917887 A1 | 10/1998 |
| EP | 0923130 A1 | 7/2001 |
| WO | WO 93/19809 A1 | 10/1993 |
| WO | WO 98/25349 A1 | 6/1998 |
| WO | WO 99/03534 A1 | 1/1999 |
| WO | WO 99/37362 A1 | 7/1999 |
| WO | WO 01/56166 A2 | 8/2001 |
| WO | WO 02/22208 A2 | 3/2002 |
| WO | WO 02/22208 A3 | 3/2002 |
| WO | WO 02/24275 A3 | 3/2002 |
| WO | WO 02/24275 A2 | 3/2002 |
| WO | WO 02/068046 A1 | 9/2002 |
| WO | WO 03/018121 A2 | 3/2003 |

OTHER PUBLICATIONS

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95–123.

Schuder, John C. et al., "Experimental Ventricular Defibrillation with an Automatic and Completely Implanted System," *Trans. Amer. Soc. Artif. Int. Organs*, vol. XVI (1970) pp. 207–212.

Schuder, John C. et al., "Transthoracic Ventricular Defibrillation in the Dog with Truncated and Untruncated Exponential Stimuli," *IEEE Transactions on Bio–Medical Engineering*, vol. BME 18, No. 6, Nov. 1971, pp. 410–415.

Tietze, U. et al., "Halbleiter–Schaltungstechnik," *Springer–Verlag*, Berlin, Germany (1991) pp. 784–786.

Walters, R.A. et al., "Analog to Digital Conversion Techniques in Implantable Devices," *Annual International Conference of the IEEE Engineering in Medicine and Biology Society*, vol. 13, No. 4 (1991) pp. 1674–1676.

* cited by examiner

SIMPLIFIED DEFIBRILLATOR OUTPUT CIRCUIT

RELATED APPLICATIONS

The invention of present application may find use in systems such as are disclosed in the U.S. patent application entitled "SUBCUTANEOUS ONLY IMPLANTABLE CARDIOVERTER-DEFIBRILLATOR AND OPTIONAL PACER," having Ser. No. 09/663,607, filed Sep. 18, 2000, pending, and U.S. patent application entitled "UNITARY SUBCUTANEOUS ONLY IMPLANTABLE CARDIOVERTER-DEFIBRILLATOR AND OPTIONAL PACER," having Ser. No. 09/663,606, filed Sep. 18, 2000, pending, of which both applications are assigned to the assignee of the present application, and the disclosures of both applications are hereby incorporated by reference.

Applications related to the foregoing applications include a U.S. patent application Ser. No. 09/940,283 entitled "DUCKBILL-SHAPED IMPLANTABLE CARDIOVERTER-DEFIBRILLATOR CANISTER AND METHOD OF USE," U.S. patent application Ser. No. 09/940,371 entitled "CERAMICS AND/OR OTHER MATERIAL INSULATED SHELL FOR ACTIVE AND NON-ACTIVE S-ICD CAN," U.S. patent application Ser. No. 09/940,468 entitled "SUBCUTANEOUS ELECTRODE FOR TRANSTHORACIC CONDUCTION WITH IMPROVED INSTALLATION CHARACTERISTICS," U.S. patent application Ser. No. 09/941,814 entitled 'SUBCUTANEOUS ELECTRODE WITH IMPROVED CONTACT SHAPE FOR TRANSTHORACIC CONDUCTION," U.S. patent application Ser. No. 09/940,356 entitled 'SUBCUTANEOUS ELECTRODE FOR TRANSTHORACIC CONDUCTION WITH HIGHLY MANEUVERABLE INSERTION TOOL," U.S. patent application Ser. No. 09/940,340 entitled 'SUBCUTANEOUS ELECTRODE FOR TRANSTHORACIC CONDUCTION WITH LOW-PROFILE INSTALLATION APPENDAGE AND METHOD OF DOING SAME," U.S. patent application Ser. No. 09/940,287 entitled "SUBCUTANEOUS ELECTRODE FOR TRANSTHORACIC CONDUCTION WITH INSERTION TOOL," U.S. patent application Ser. No. 09/940,377 entitled "METHOD OF INSERTION AND IMPLANTATION FOR IMPLANTABLE CARDIOVERTER-DEFIBRILLATOR CANISTERS," U.S. patent application Ser. No. 09/940,599 entitled "CANISTER DESIGNS FOR IMPLANTABLE CARDIOVERTER-DEFIBRILLATORS," U.S. patent application Ser. No. 09/940,373 entitled "RADIAN CURVE SHAPED IMPLANTABLE CARDIOVERTER-DEFIBRILLATOR CANISTER," U.S. patent application Ser. No. 09/940,273 entitled "CARDIOVERTER-DEFIBRILLATOR HAVING A FOCUSED SHOCKING AREA AND ORIENTATION THEREOF," U.S. patent application Ser. No. 09/940,378 entitled "BIPHASIC WAVEFORM FOR ANTI-BRADYCARDIA PACING FOR A SUBCUTANEOUS IMPLANTABLE CARDIOVERTER-DEFIBRILLATOR," and U.S. patent application Ser. No. 09/940,378 entitled "BIPHASIC WAVEFORM FOR ANTI-TACHYCARDIA PACING FOR A SUBCUTANEOUS IMPLANTABLE CARDIOVERTER-DEFIBRILLATOR,"

FIELD OF THE INVENTION

The subject invention relates generally to electronic circuitry and finds particular application in defibrillator circuitry.

BACKGROUND OF THE INVENTION

Defibrillation/cardioversion is a technique employed to counter arrhythmic heart conditions including some tachycardias in the atria and/or ventricles. Typically, electrodes are employed to stimulate the heart with electrical impulses or shocks, of a magnitude substantially greater than pulses used in cardiac pacing.

Defibrillation/cardioversion systems include body implantable electrodes that are connected to a hermetically sealed container housing the electronics, battery supply and capacitors. The entire system is referred to as implantable cardioverter/defibrillators (ICDs). The electrodes used in ICDs can be in the form of patches applied directly to epicardial tissue, or, more commonly, are on the distal regions of small cylindrical insulated catheters that typically enter the subclavian venous system, pass through the superior vena cava and, into one or more endocardial areas of the heart. Such electrode systems are called intravascular or transvenous electrodes. U.S. Pat. Nos. 4,603,705, 4,693,253, 4,944,300, 5,105,810, the disclosures of which are all incorporated herein by reference, disclose intravascular or transvenous electrodes, employed either alone, in combination with other intravascular or transvenous electrodes, or in combination with an epicardial patch or subcutaneous electrodes. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active can electrode and therefore it has no practical use. It has in fact never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353, 5,261,400, 5,620,477, and 5,658,321 the disclosures of which are incorporated herein by reference.

ICDs are now an established therapy for the management of life threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, especially children at risk of cardiac arrest, the requirement of ICD therapy to use intravenous catheters and transvenous leads is an impediment to very long term management as most individuals will begin to develop complications related to lead system malfunction sometime in the 5–10 year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, are not without their chronic patient management limitations in those with life expectancies of >5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of a related therapy, the automatic external defibrillator (AED). AEDs employ the use of cutaneous patch electrodes, rather than implantable lead systems, to effect defibrillation under the direction of a bystander user who treats the patient suffering from V-Fib with a portable device containing the necessary electronics and power supply that allows defibrillation. AEDs can be nearly as effective as an ICD for defibrillation if applied to the victim of ventricular fibrillation promptly, i.e., within 2 to 3 minutes of the onset of the ventricular fibrillation.

AED therapy has great appeal as a tool for diminishing the risk of death in public venues such as in air flight. However, an AED must be used by another individual, not the person suffering from the potential fatal rhythm. It is more of a public health tool than a patient-specific tool like an ICD. Because >75% of cardiac arrests occur in the home, and over half occur in the bedroom, patients at risk of cardiac arrest are often alone or asleep and can not be helped in time with an AED. Moreover, its success depends to a reasonable degree on an acceptable level of skill and calm by the bystander user.

What is needed therefore, especially for children and for prophylactic long term use for those at risk of cardiac arrest, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years.

Circuitry for controlling so-called "high side" switches in defibrillator circuitry has exhibited considerable complexity, necessitating use, for example, of transformers, optocouplers and/or photo voltaic generators. Such complexity is generally undesirable and particularly undesirable in devices intended for implantation within the human body.

SUMMARY

According to one aspect of the invention, high side defibrillator driver circuitry is provided which employs silicon controlled rectifiers serving as high side switches. Applying a control current to a selected gate of one of the high side SCR's turns on that SCR. According to another aspect of the invention, positive turn-on of the high side SCRs is ensured by inserting a constant current source into the low side activation current path at start-up.

DETAILED DESCRIPTION OF ILLUSTRATIVE EMBODIMENTS

Figure 1:
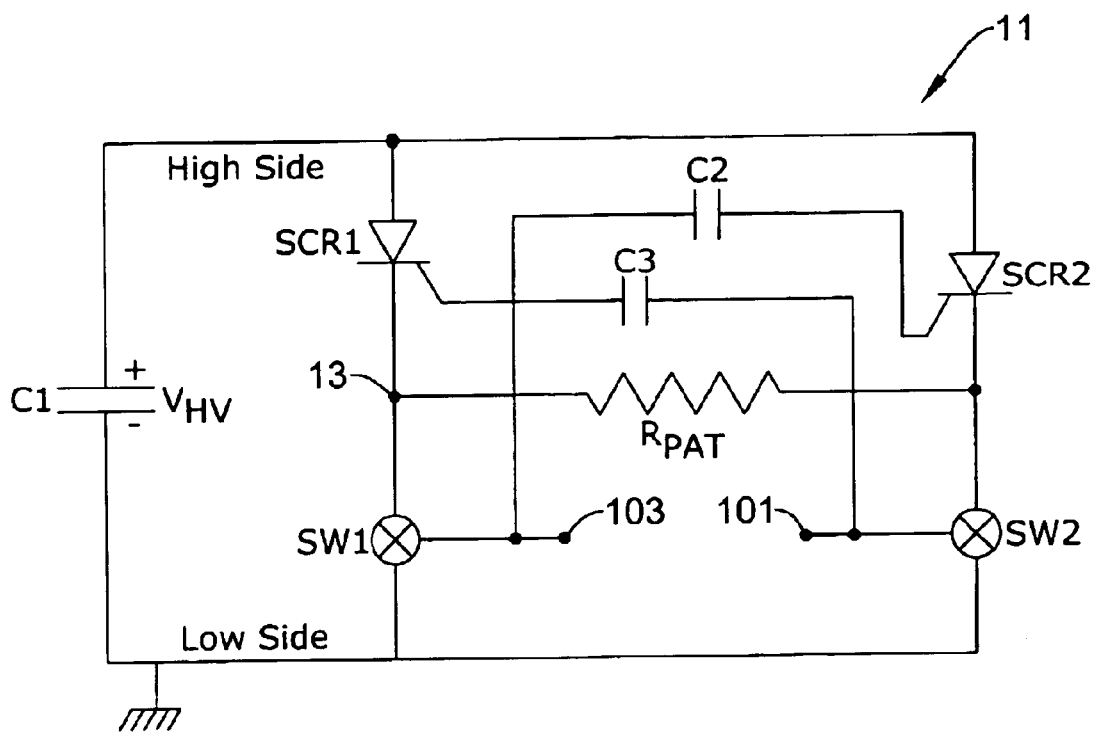
FIG. 1 is an electrical circuit schematic of a circuit according to a first illustrative embodiment of the invention.

FIG. 1 illustrates an electrical circuit including a first illustrative embodiment according to the invention. The circuit includes a high voltage capacitor $C_1$ grounded at one terminal and connected at its opposite terminal to respective anodes of two silicon controlled rectifiers $SCR_1$, $SCR_2$.

The respective cathodes of the respective rectifiers $SCR_1$, $SCR_2$ are connected to respective first terminals of first and second low side switches $SW_1$, $SW_2$. The respective cathodes of the silicon controlled rectifiers $SCR_1$, $SCR_2$ are additionally electrically coupled to respective physical locations on a patient on either side of a patient resistance denoted $R_{PAT}$.

The gate or trigger terminal of the first silicon controlled rectifier $SCR_1$ is connected through a capacitor $C_3$ to a first terminal 101 of the second switch $SW_2$. The gate or trigger terminal of the second silicon controlled rectifier $SCR_2$ is connected through a second capacitor C2 to the first terminal 103 of the first low side switch $SW_1$. Respective second terminals of the switches $SW_1$, $SW_2$ are connected to ground in the embodiment illustrated in FIG. 1.

The respective first terminals 103, 101 of the respective low side switches $SW_1$, $SW_2$ are those which, in response to application of a switching signal, cause the switches $SW_1$, $SW_2$ to close. Hence, the first terminals 101, 103 may comprise, e.g., the gates of respective switching transistors or respective SCRs.

Figure 2:
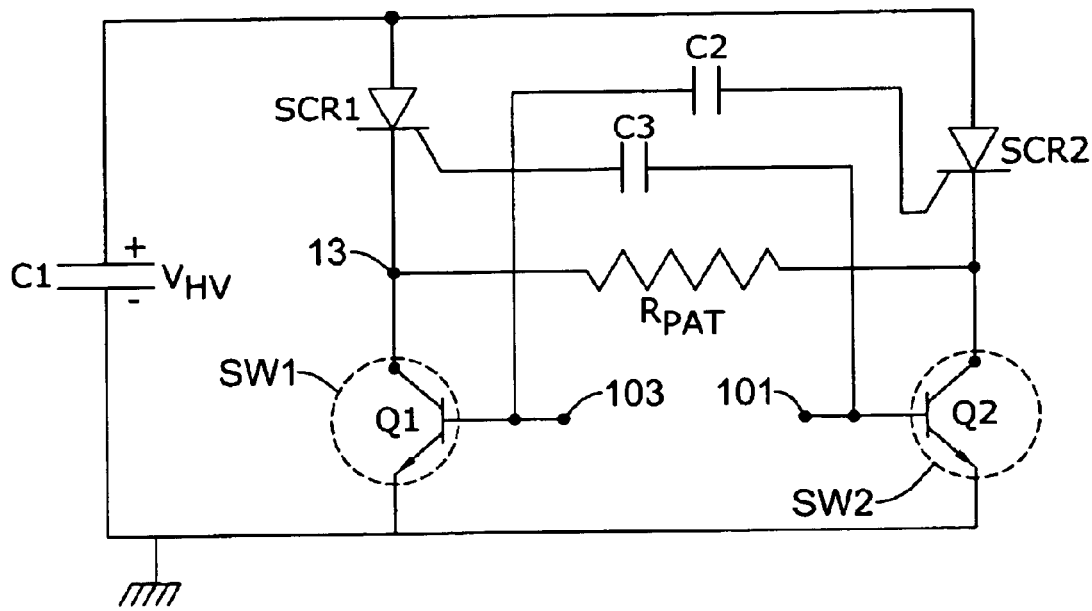
FIG. 2 illustrates the use of low side transistor switches within a circuit like that of FIG. 1.

The embodiment of FIG. 2 particularly illustrates respective transistors $Q_1$, $Q_2$ used as the switching devices in a circuit according to FIG. 1. These transistors may be, for example, IGBTs or MOSFETs. The switches $SW_1$, $SW_2$ can also comprise silicon controlled rectifiers (SCRs).

To illustrate operation of the circuit of FIG. 1, assume a control voltage signal is applied to the first terminal 101 of the second switch $SW_2$. Such application closes the switch $SW_2$ and creates a current through the coupling capacitor $C_3$ into the gate of the first silicon controlled rectifier $SCR_1$, which current turns on $SCR_1$. Activation of the first silicon controlled rectifier $SCR_1$ applies a voltage to the patient resistance $R_{PAT}$ and causes a current to flow through $SCR_1$, $R_{PAT}$, and $SW_2$ to ground. In one application, this current may be terminated by appropriately turning off the switch $SW_2$ to thereby create a monophasic waveform.

To create a biphasic waveform, the switch $SW_2$ is opened for a selected interval, and a control voltage signal is then applied to the first terminal 103 of the first switch $SW_1$. This control voltage signal closes the switch $SW_1$ and creates a drive current into the gate of the second silicon controlled rectifier $SCR_2$, thereby turning $SCR_2$ "on." A current path is thus created from the high voltage capacitor $C_1$ through $SCR_2$, the patient resistance $R_{PAT}$, and the switch $SW_1$, resulting in a negative going pulse, i.e., the second phase of a biphasic waveform.

The circuit of FIG. 1 has a drawback in that it exhibits an extremely rapid change of current with respect to time ("dI/dt"), which may present control problems. Another drawback is that it takes a finite amount of time for the second switch $SW_2$ to come "on," which presents the possibility that the SCR1 will not turn on because a silicon controlled rectifier typically requires a certain amount of current flow through it in order to maintain the "on" state. In such case, the circuit will not switch correctly.

Figure 3:
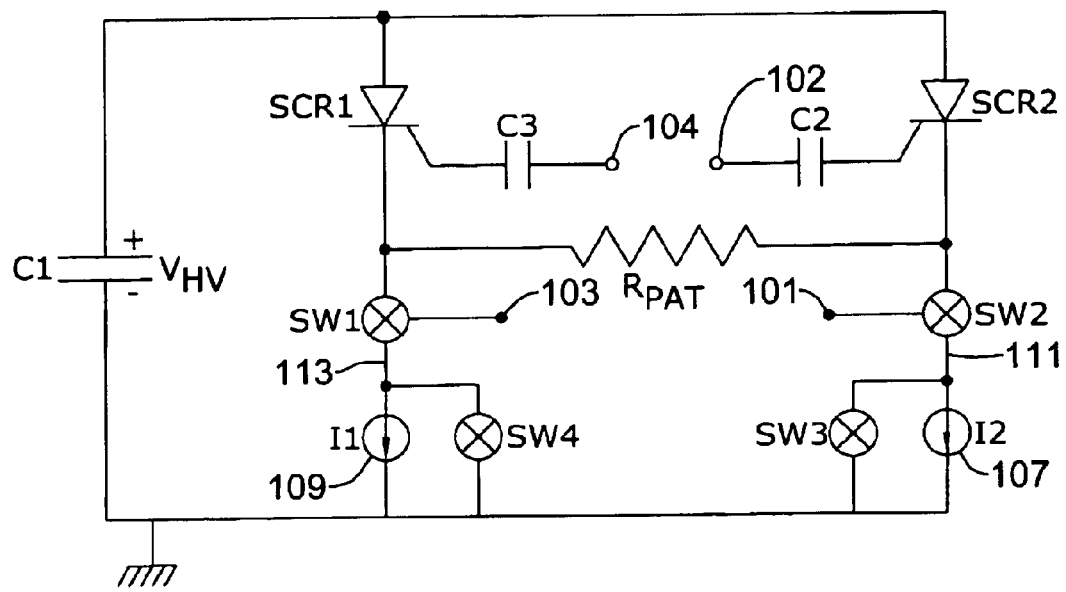
FIG. 3 is an electrical circuit schematic of a second illustrative embodiment.

The embodiment of FIG. 3 improves over those of FIGS. 1 and 2 by providing positive control of switching of the silicon controlled rectifiers $SCR_1$, $SCR_2$ by causing the low side switches $SW_1$, $SW_2$ to operate as current sources.

Thus, in the embodiment of FIG. 3, the capacitors $C_2$, $C_3$ are arranged to have control signals selectively applied to respective terminals 102, 104, which are not connected to the first terminals 101, 103, e.g., gates, of the switching devices $SW_1$, $SW_2$. Additionally, respective constant current source circuits 107, 109 are created in the respective lower legs 111, 113 of the switches $SW_1$, $SW_2$. Third and fourth switches $SW_3$, $SW_4$ are provided to selectively short out the respective constant current sources 107, 109, i.e., create a short circuit around them to ground.

With respect to the operation of the circuit of FIG. 3, various components are selectively activated ("turned on") in order to deliver a monophasic pulse, if desired, or both phases of a biphasic waveform. In order to create a monophasic pulse, for example, the switch $SW_2$ is turned on and enabled to work as a current source. Then the gate of $SCR_1$ is pulsed with a signal applied to the first terminal 104 of the capacitor $C_3$. Once the pulse triggers $SCR_1$, $SCR_1$ is guaranteed to stay on because the current source 107 is activated to supply an amount of current selected to hold $SCR_1$ on.

Figure 4:
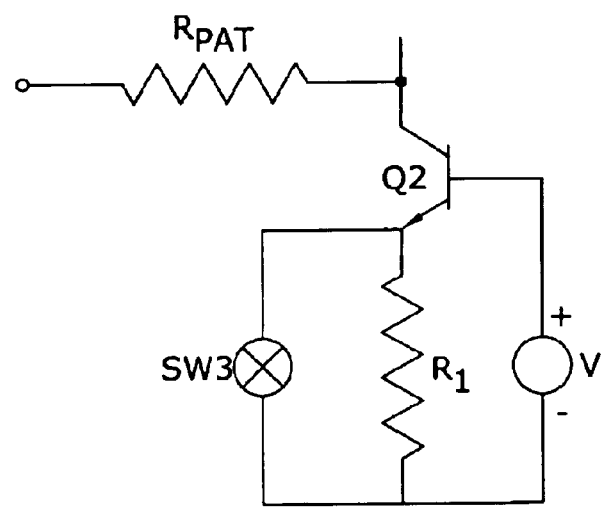
FIG. 4 is an electrical circuit schematic of a current source employable in the circuit of FIG. 3.

An example of a current source circuit 107, 109 is illustrated in FIG. 4, where the transistor $Q_2$ functions as one of the low side switches $SW_1$, $SW_2$ of FIG. 3. The constant voltage applied across the resistor $R_1$ may be supplied, for example, by a digital to analog converter or other techniques including those shown and described in co-pending application Ser. No. 10/011,955 by this inventor entitled Defibrillation Pacing Circuitry filed Nov. 5, 2001 and incorporated by reference herein.

The current supplied by the current sources 107, 109 can be programmed to any desired amount, e.g., anywhere between 10 to 500 milliamps, but is particularly set to the value of the holding current required by $SCR_1$. Thus, for example, if the holding current is 100 milliamps, the current through $R_{PAT}$ rises from 0 to 100 milliamps very quickly, but only to 100 milliamps. Thus, dI/dt is fairly limited.

At that point (100 ma), the monophase pulse is initiated by turning on the first silicon controlled rectifier $SCR_1$. As soon as $SCR_1$ turns on, the current source 107 is switched out of the circuit, e.g., by creating a short across the resistance $R_1$ of FIG. 4, which results in a very high current ($\cong V_{HV}/R_{pat}$) with the dI/dt and the dV/dt being controlled by the controlled slew rate of the turn-on and turn-off time of the drive signal. To truncate the monophase pulse, the low side switch $SW_2$ is then turned off, the current goes to 0, and the silicon controlled rectifier $SCR_1$ turns off.

In order to create the second phase of a biphasic waveform, a similar procedure is followed. The switch $SW_1$ is enabled, e.g., by application of a 15 volt pulse with respect to ground, as is the current source $I_1$ in its leg. Then, via the capacitive coupling provided by the capacitor $C_2$, the second silicon controlled rectifier $SCR_2$ is triggered, for example, by application of a 15 volt pulse with respect to ground, but only to the programmed holding current provided via the current source 109. Next, the current source 109 is removed and the current through $R_{PAT}$ ramps up in a controlled manner by controlling the slew rate of the drive signal to create the second phase of the biphasic waveform.

As those skilled in the art will appreciate, the illustrative embodiments employ a high side bridge wherein the drivers each include only two components, the SCRs and the respective capacitors $C_2$, $C_3$. The control voltages applied to the capacitors may range from, for example, 5 to 15 volts. Thus, the high side driver circuitry has been made smaller, simpler, with fewer components. As those skilled in the art appreciate, SCRs are typically smaller devices than IGBTs or MOSFETs, resulting in an even more efficient use of silicon. In addition to these advantages, the dV/dt and the dI/dt are controllable.

While the present invention has been described above in terms of specific embodiments, it is to be understood that the invention is not limited to the disclosed embodiments. On the contrary, the following claims are intended to cover various modifications and equivalent methods and structures included within the spirit and scope of the invention.

What is claimed is:

1. In a defibrillator circuit, the method comprising:
   using first and second silicon controlled rectifiers as high side switch devices; and
   employing capacitors cross-coupled to respective low side switching devices to switch "on" the respective silicon controlled rectifiers.

2. The method of claim 1 wherein said defibrillator circuit forms part of a subcutaneous only implantable cardioverter-defibrillator.

3. In a defibrillator circuit, the method comprising:
   using first and second silicon controlled rectifiers as high side switching devices; and
   applying a switching signal to the respective gates of each of said first and second silicon controlled rectifiers through a first and second capacitors respectively coupled to said gates.

4. A method of controlling high side switching in a defibrillation circuit having a high side for providing current to a patient and a low side for receiving current from the patient, comprising:
   employing a first silicon controlled rectifier having first control terminal as a high side switching component; and
   employing a first device coupled to said first control terminal to create a current into said first control terminal;
   wherein said first device comprises a capacitor.

5. The method of claim 4 further including the step of employing a second silicon controlled rectifier having a second control terminal as a second high side switching device and employing a second device coupled to said second control terminal to create a current into said second control terminal.

6. The method of claim 4 wherein each of said first and second control terminals are adapted to receive a control current, said control current causing closing of a signal path through the respective rectifier.

7. The method of claim 5 further wherein said second device comprises a capacitor.

8. The method of claim 5 wherein said first and second silicon controlled rectifiers each have a respective terminal configured for applying a therapeutic signal across a patient.

9. The method of claim 8 further including the step of applying a therapeutic signal to each of said first and second silicon controlled rectifiers.

10. The method of claim 9 wherein said therapeutic signal is applied to respective anodes of the first and second silicon controlled rectifiers.

11. The method of claim 10 wherein the respective cathodes of the first and second silicon controlled rectifiers are configured to convey said therapeutic signal to the patient. patient.

12. The method of claim 5 further including the step of employing first and second low side switches, the first low side switch having a first leg connected to said first silicon controlled rectifier, the second low side switch having a leg connected to said second silicon controlled rectifier.

13. The method of claim 12 further including the step of causing a current to pass through said first silicon controlled rectifier to said patient and from said patient through said second switch.

14. The method of claim 12 further including the steps of causing a current to pass through said second silicon controlled rectifier to said patient and from said patient through said second switch.

15. The method of claim 13 further including the step of generating a current to positively hold "on" said first silicon controlled rectifier.

16. The method of claim 4 further including the step of generating a current to positively hold "on" said first silicon controlled rectifier.

17. The method of claim 15 wherein a constant current source is used to generate said current.

18. The method of claim 16 wherein a constant current source is used to generate said current.

19. The method of claim 4 wherein said defibrillator circuit forms part of a subcutaneous only implantable cardioverter-defibrillator.

20. A defibrillator circuit having a high side for delivering current to a patient and a low side for receiving current from a patient comprising:
   a first high side switching device having a control terminal adapted to receive a control current, said control current causing closing of a signal path through said switching device;
   a first capacitor coupled to said control terminal and adapted to receive a control voltage selected to crease said control current;
   a second high side switching device having a control terminal adapted to receive a control current, said control current causing closing of a signal path through said switching device; and
   a second capacitor coupled to the control terminal of said second high side switching device and adapted to receive a control voltage selected to create said current.

21. The circuit of claim 20 wherein said first high side switching device comprises a first silicon controlled rectifier.

22. The circuit of claim 20 wherein said second high side switching device comprises a second silicon controlled rectifier.

23. The circuit of claim 22 wherein said first and second silicon controlled rectifiers each have a respective terminal configured for applying a voltage across a patient.

24. The circuit of claim 23 further including a drive circuit adapted to apply a drive voltage to each of said first and second silicon controlled rectifiers.

25. The circuit of claim 24 wherein said drive voltage is applied to respective anodes of the first and second silicon controlled rectifiers.

26. The circuit of claim 23 wherein respective cathodes of the first and second silicon controlled rectifiers are adapted to apply said voltage across said patient.

27. The circuit of claim 24 further including first and second low side switches, the first low side switch having a first leg connected to said first silicon controlled rectifier, said second low side switch having a leg connected to said second silicon controlled rectifier.

28. The circuit of claim 27 further including means for causing a current to pass through said first silicon controlled rectifier to said patient and from said patient through said second switch.

29. The circuit of claim 27 further including means for causing a current to pass through said second silicon controlled rectifier to said patient and from said patient through said first switch.

30. The circuit of claim 28 wherein said means includes means for generating a current to positively hold "on" said first silicon controlled rectifier.

31. The circuit of claim 30 wherein said means for generating a current comprises a constant current source.

32. The circuit of claim 29 wherein said means for causing a current to pass through said second silicon controlled rectifier includes means for generating a current to positively hold "on" said first silicon controlled rectifier.

33. The circuit of claim 32 wherein said means for generating comprises a constant current source.

34. The method of claim 27 wherein said first and second low side switches each comprise one of a (a) silicon controller rectifier, (b) MOSFET, or (c) IGBT.

35. A defibrillator circuit having a high side for delivering current to a patient and a low side for receiving current from a patient comprising:
   a first high side switching device having a control terminal adapted to receive a control current, said control current causing closing of a signal path through said switching device; and
   a first capacitor coupled to said control terminal and adapted to receive a control voltage selected to create said control current;
   wherein said first high side switching device comprises a first silicon controlled rectifier.

36. The circuit of claim 35 wherein said control terminal is the gate of a first silicon controlled rectifier.

37. The circuit of claim 35 further including a current source located in said circuit and selectively activatable for holding said silicon controlled rectifier "on" during a selected interval.

38. The circuit of claim 37 wherein said current source is connected to a leg of a low side switch of said circuit.

39. The circuit of claim 35 further including a second high side switching device having a control terminal adapted to receive a control current, said control current causing closing of a signal path through said switching device.

40. The apparatus of claim 35 wherein said defibrillator circuit forms part of a subcutaneous only implantable cardioverter-defibrillator.

* * * * *

UNITED STATES PATENT AND TRADEMARK OFFICE
CERTIFICATE OF CORRECTION

PATENT NO.    : 6,954,670 B2
DATED         : October 11, 2005
INVENTOR(S)   : Alan H. Ostroff It is certified that error appears in the above-identified patent and that said Letters Patent is hereby corrected as shown below:

Column 1,
Line 62, after "CARDIOVERTER-DEFIBILLATOR," insert -- the disclosures of which applications are hereby incorporated herein by reference --.

Column 5,
Line 34, after "voltage" and before "applied", insert -- V --.

Column 7,
Line 4, after "patient.", delete "patient.".
Line 39, delete "crease", and insert therefor -- create --.

Signed and Sealed this

Thirteenth Day of December, 2005

JON W. DUDAS
*Director of the United States Patent and Trademark Office*